(12) United States Patent
Auger et al.

(10) Patent No.: US 7,939,323 B2
(45) Date of Patent: May 10, 2011

(54) METHOD OF ISOLATING CELLS FROM UMBILICAL CORD

(75) Inventors: Francois A. Auger, Quebec (CA); Lucie Germain, Saint-Augustin (CA); Murielle Remy-Zolghadri, Le Bouscat (FR); Cindy J. Hayward, Sainte-Roy (CA)

(73) Assignee: Universite Laval, Quebec (CA)

( * ) Notice: Subject to any disclaimer, the term of this patent is extended or adjusted under 35 U.S.C. 154(b) by 532 days.

(21) Appl. No.: 11/924,661

(22) Filed: Oct. 26, 2007

(65) Prior Publication Data

US 2008/0102522 A1 May 1, 2008

Related U.S. Application Data

(63) Continuation of application No. 11/314,153, filed on Dec. 21, 2005, now abandoned, which is a continuation of application No. PCT/CA03/00979, filed on Jun. 27, 2003.

(51) Int. Cl.
*C12N 5/00* (2006.01)
*C12N 5/02* (2006.01)
*C12N 5/07* (2010.01)
*A01N 63/00* (2006.01)

(52) U.S. Cl. ........ 435/378; 435/366; 435/377; 435/325; 424/93.1; 424/93.21; 424/93.7

(58) Field of Classification Search .................. 435/325, 435/366, 377, 378; 424/93.1, 93.21, 93.7
See application file for complete search history.

(56) References Cited

U.S. PATENT DOCUMENTS

| | | | |
|---|---|---|---|
| 5,134,065 A | 7/1992 | Sanzo et al. | |
| 5,919,702 A | 7/1999 | Purchio et al. | |
| 7,045,148 B2 * | 5/2006 | Hariri | 424/529 |
| 2002/0045260 A1 | 4/2002 | Hung et al. | |

FOREIGN PATENT DOCUMENTS

| | | |
|---|---|---|
| JP | 2000139454 | 5/2000 |
| WO | 98/17791 A1 | 4/1998 |
| WO | 99/01538 A1 | 1/1999 |
| WO | 99/54439 A1 | 10/1999 |
| WO | 00/73421 A2 | 12/2000 |
| WO | 02/036751 A2 | 5/2002 |
| WO | 02/46373 A1 | 6/2002 |
| WO | 02/066470 A1 | 8/2002 |
| WO | 02/083262 A1 | 10/2002 |

OTHER PUBLICATIONS

Auger, F.A. et al; Ernst Schering Research Foundation Workshop, No. 35:73-88 (2002).
Germain, L. et al.; Medical & Biological Engineering & Computing; 38(2):232-240 (2000).
Grenier, G. et al.; In Vitro Cellular & Developmental Biology Animal; 39(3-4):131-139 (2003).
Jaffe, E.A. et al.; The Journal of Clinical Investigation; 52(11):2745-2756 (1973).
L'Heureux, N. et al.; The FASEB Journal; 15(2):515-524 (2001).
Nanaev, A.K. et al.; Placenta; 18(1):53-64 (1997).
Ross, Russell; The Journal of Cell Biology; 50(1):172-186 (1971).
Gudrun, Ulrich-Merzenich et al. "Simultaneous isolation of endothelial and smooth muscle cells from human umbilical artery or vein and their growth response to low-density lipoproteins", In Vitro Cell. Dev. Bio.—Animal 38:265-272, May 2002.
Coskunfirat, O. Koray et al. "Microvascular Free Tissue Transfer for Treatment of Osteoradionecrosis of the Maxilla", Plastic and reconstructive surgery, 115(1):54-60, Jan. 2005.
Chow, Lawrence C. et al., "Vascular Mapping of the Leg with Multi-Detector Row CT Angiography prior to Free-Flap Transplantation" Vascular and Interventional Radiology, 237(1)353-360, Oct. 2005.
Sarugaser, Rahul et al., "Human Umbilical Cord Perivascular (HUCPV) Cells: A Source of Mesenchymal Progenitors," Stem Cells, 23:220-229, 2005.
Wang, Hwai-Shi et al. "Mesenchymal Stem Cells in the Wharton's Jelly of the Human Umbilical Cord", Stem Cells, 22:1330-1337, 2004.
Mitchell, Kathy E. et al. "Matrix Cells from Wharton's Jelly Form Neurons and Glia", Stem Cells, 21:50-60, 2003.
Sanmano, Borisut et al. "Engraftment of umbilical cord epithelial cells in athymic mice: in an attempt to improve reconstructed skin equivalents used as epithelial composite", Journal of Dermatological Science, 37:29-39, 2005.
Parry, E.W. "Some electron microscope observations on the mesenchymal structures of full-term umbilical cord", J. Anat. 107(3):505-518, 1970.
Takechi, Kimihiro et al. "Ultrastructural and Immunohistochemical Studies of Wharton's Jelly Umbilical Cord Cells", Placenta, 14:235-245, 1993.
Schwartz, Seymour I. et al. "Plastic and Reconstructive surgery", Principles of Surgery, 43 : 996-997, 2007.
Pelletier, Bernard et al. "Cultures primaires de cellules épithéliales et cultures à long terme de fibroblastes à partir du cordon ombilical humain : caractérisation ultrastructurale et immunocytochimique", C. R. Soc. Biol. 180:447-459, 1986.
Disa, J. J. et al. "Reconstruction of lateral skull base oncological defects: the role of free tissue transfer", Ann Plast Surg., 41(6):633-639, Dec. 1998.

(Continued)

*Primary Examiner* — Maria Leavitt
(74) *Attorney, Agent, or Firm* — Nixon Peabody, LLP (57) ABSTRACT

The present invention relates a method for isolating four cell types from a single umbilical cord as pure cultures. These cell lines (epithelial cells, fibroblasts, smooth muscle cells and endothelial cells) can be characterized and utilized in experimental models and for therapeutic purposes. Particularly, the umbilical cells isolated herein are used to form a tissue replacement or engineered living composition. Also, the isolated umbilical cells of the invention may have the potential of progenitor cells.

7 Claims, 5 Drawing Sheets

OTHER PUBLICATIONS

Zeng B. et al. "Application of free flaps in combined transplantation", Zhongguo Xiu Fu Chong Jian Wai Ke Za Zhi, 19 (7):508-510, Jul. 2005 (abstract only).

McElreavey, K.D. et al. "Isolation, culture and characterisation of fibroblast-like cells derived from the Wharton's jelly portion of human umbilical cord" Biochem Soc. Trans. 19(1) 295, 1991.

* cited by examiner

METHOD OF ISOLATING CELLS FROM UMBILICAL CORD

CROSS-REFERENCE TO RELATED APPLICATIONS

This application is a Continuation under 35 U.S.C. §120 of U.S. Ser. No. 11/314,153, filed Dec. 21, 2005, now abandoned, which is a Continuation under 35 U.S.C. §120 of International Application No. PCT/CA03/00979, filed Jun. 27, 2003, which designates Canada.

TECHNICAL FIELD

The present invention relates to a method for isolating four cell types from the umbilical cord, and more particularly from the umbilical vein, in good conditions without having to execute separate methods for each type of cell. The method is of particular importance for obtaining a variety of different cells in good condition from only one tissue.

BACKGROUND ART

Despite the diversity of the nature, morphology, characteristics and function of isolated animal cells, it is presently generally admitted that these cells are derived from a single cell population, termed "stem cells". Unlike more mature or differentiated cells, stem cells are capable of self-regeneration but may also divide into progenitor cells that are no longer pluripotent nor capable of self-regeneration. These progenitor cells divide repeatedly to form more mature cells, which eventually become terminally differentiated to form various mature cells. Thus the large number of mature cells is derived from a small reservoir of stem cells by a process of proliferation and differentiation.

In the particular domain of blood vessels, one promising solution to the problems associated with synthetic-based replacement tissues, such as vascular grafts, is to assemble blood vessels in vitro using only the patient's own cells and then re-implant them into the patient. In theory, tissue-engineered blood vessels should provide mechanically stable vessels built only from autologous tissue, therefore generating no immune responses. Tissue engineering has been used successfully in the past to build less complex structures such as skin, but has had only relative success with other three-dimensional tissues and organs such as tissue-engineered blood vessels. Common problems associated with three-dimensional engineered tissues include the complexity of reconstruction, the lack of structural integrity and mechanical strength, and the need for biologically active tissues. This is a particular problem for tissue-engineered blood vessels, since these vessels will be subjected to significant mechanical loads both from blood pressure (which may be abnormally high in patients with heart disease), as well as from the relative motion between the anchoring sites of the vessel. Moreover, the tissue-engineered blood vessels must demonstrate sufficient stability and tear resistance to allow surgical handling and implantation, and require a biologically active endothelial layer.

An important cause of these problems seems to be associated with the sources of the cells used to prepare engineered blood vessels or other replacement tissues. In fact, most methods available at the moment allow the isolation of a maximum of two cell types from a single tissue, which should be preferentially autologous. Also, these cells, alone or mixed with other cell types, are generally mature and well differentiated, which constitutes a limiting factor when a certain level of flexibility and adaptability is necessary in constructing an engineered replacement tissue.

Stem cells mature into progenitor cells and then become lineage committed, that is, incapable of maturing into all of the different lineages which the stem cell is capable of producing. Highly purified populations of stem cells currently find use in the long-term repopulation of particular body systems. Purified progenitor cells of individual lineages would find use only in transiently repopulating or augmenting the various lineages. As progenitors are not believed to be self-regenerating, the repopulation or augmentation would be limited, for example, to short-term tissue-specific reconstitution.

The field of tissue engineering uses living cultured human or animal cells from various sources to reconstruct functional tissues and organs for experimental and therapeutic purposes.

Medical applications of umbilical haematopoietic cord stem cells are becoming well known both in and out of the medical community.

As a result of the successful clinical experiences and the large number of people who have benefited from the medical uses of cord haematopoietic stem cells to date (or who will benefit from cord stem cell uses in the future), different cord stem cell preparations are presently under investigation.

The use of the pluripotentiality of lineage-committed progenitor cells circumvents many of the problems that would arise from the transfer of mature cells. However, such progenitor cells may have to be separated through carrying out parallel methods upon different sources of living tissues. Separation requires identification of the cells and characterization of phenotypic differences that can be utilized in a separation procedure. In addition, the methods known at this time for preparing replacement tissues still have to be carried out with cells originating from heterologous sources, therefore creating problems of compatibility in using such replacement tissues.

However, the cells originating from the umbilical cord tissue remain underused both as progenitor cells, and in complex cell compositions for the preparation of replacement and engineered tissues.

Considering the state of the art described herein, there is still a need for single sources of multiple cell types for the preparation of progenitor cells or replacement cells or tissues. Moreover, there still exist no complex cell compositions capable of being completely compatible when reintroduced into a human or animal body.

SUMMARY OF THE INVENTION

According to one aspect of the present invention, there is provided a method for the simultaneous isolation of four cell types from one umbilical cord sample comprising the steps of:

a) isolating endothelial cells by perfusing the vein of an umbilical cord biopsy with a solution comprising thermolysin for a period of time to allow detachment of said endothelial cells from said vein;

b) treating said umbilical cord biopsy of step a) with a solution of trypsin-EDTA for a time sufficient to allow detachment of epithelial cells;

c) mechanically removing smooth muscle cells and fibroblast-like cells from said umbilical cord biopsy followed by a culture period of sufficient time to allow separation and isolation of smooth muscle and fibroblast-like cells from laminae; and d) harvesting the isolated cells of steps a) to c).

The invention also provides for the use of the above-mentioned four cell types for the preparation of a replacement or engineered tissue or graft.

The invention additionally relates to a biological composition comprising these four cell types.

For the purpose of the present invention the following terms are defined below.

The terms "progenitor" or "progenitor cells" as used herein are intended to indicate cell populations which are no longer stem cells but which have not yet become terminally differentiated or which still have a certain level of flexibility and adaptability.

DISCLOSURE OF THE INVENTION

The present invention will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

In accordance with the present invention, a method is provided for isolating four cell types from only one umbilical cord section in successive steps allowing each cell type to be kept in good physiological condition after each isolation step.

The advantage of the present invention over the prior art will be recognized as providing a method allowing the preparation of four umbilical cell types in which after each step, all the desired types of cells are kept alive and in condition to be harvested for further uses. No equivalent techniques in the art are known to allow a skilled person to isolate four cell types from a single tissue biopsy without significant cell mortality and tissue destruction.

The inventors have developed a method for the extraction of four distinct cell types from a single umbilical cord biopsy or section. This permits the conservation of multiple cell types from a unique source, or from only one person, for present or future therapeutic applications, and this also permits research using tissue models fabricated with cells of the same lineage.

In a preferred embodiment of the invention, autologous cells are harvested from the patient's own body to eliminate the risks of disease transmission and tissue rejection. All umbilical cord biopsies contain endothelial cells, epithelial cells, smooth muscle cells, and fibroblasts. Therefore, almost any biopsy procedure or tissue harvest will provide a suitable starting point for the four of them.

The umbilical cord is of particular interest as a source of cell lines because of its foetal condition, and because its obtention is simple and non-invasive. The present invention is directed to a method for the extraction of four cell types: epithelial cells, fibroblasts, smooth muscle cells and endothelial cells, as pure cultures from a single human umbilical cord.

The human umbilical cord is a foetal structure that carries blood from the foetal circulation to the placenta for oxygenation via the two umbilical arteries, and returns the oxygenated blood to the developing child by way of the umbilical vein. The blood vessels are lined with endothelial cells, which are in turn surrounded by a substantial layer of smooth muscle cells (SMC), thicker around the arteries than around the vein. There is a rather loosely defined adventitial layer of fibroblasts encircling the SMC. The bundle of blood vessels is enclosed in turn by a thick layer of extracellular matrix sparsely populated by fibroblasts and known as Wharton's jelly. A thin layer of epithelial cells covers the outer surface of the umbilical cord.

The umbilical cord epithelium is formed of a thin layer of epithelial cells resting on a basement membrane, and is the only part of the umbilical cord to be in contact with the surrounding amniotic fluid, thus acting as a barrier between the internal tissues and the outer liquid. It is often only a single cell layer thick, but regions of up to five layers of thickness do occur. The epithelium of the cord is contiguous both with the amniotic epithelium, from which it is derived in the early stages of development, as well as with the early embryonic periderm and the later foetal epithelium. The morphology of the umbilical cord epithelium has been described as being closely related to the early foetal epidermis before its keratinisation. This process does not occur normally in the umbilical cord epithelium except in the region adjacent to the foetus, the rest of the epithelium remaining as a simple squamous epithelium. The epithelial cells are tightly joined to each other by numerous desmosomes, and to the underlying basement membrane by hemidesmosomes. The dense cytoskeleton contains keratin fibres of many types, the presence of which is typical of epithelia. Few studies have been done to further characterize these cells.

The connective tissue of the umbilical cord, commonly called Wharton's jelly, consists of fibroblasts dispersed within a loose mucous connective tissue, composed mainly of a network of collagen fibres and a ground substance of glycosaminoglycans, mostly hyaluronic acid, along with an independent fibrillar network of glycoprotein microfibrils. This tissue serves to protect the umbilical blood vessels from compression and torsion. The fibroblasts themselves are somewhat unusual as they combine characteristics of both typical fibroblastic cells (abundant Golgi apparati, collagen secretion granules, mitochondria and rough endoplasmic reticulae) and of smooth muscle cells (deeply indented nuclei, pinocytotic vesicles and fibronexus junctions). Their content of α-smooth muscle actin gives them a certain contractility. Desmin and non-muscle myosin have also been identified as intracellular components. There is disagreement on the exact nature and origin of these cells because of their diverse characteristics, and further analysis will be necessary to shed light on their exact role.

Smooth muscle cells form the ring-shaped media that surround the arteries and vein of the umbilical cord. Their main function is contraction, but these cells are also capable of many other functions when required, including production of extracellular matrix proteins and increased cell proliferation.

Typical components of the smooth muscle cell include smooth muscle actin, myosin, calponin, caldesmon, vinculin, tropomyosin, vimentin and desmin. Many and varied ion channels and membrane receptors allow sensitive regulation of the contractile behaviour of these cells. Smooth muscle cells derived from the umbilical cord have been extensively used in the study of smooth muscle cells, their metabolism and their characteristics, as well as in tissue reconstructions.

The umbilical cord vein and arteries are lined by endothelial cells, which have many diverse functions in the body, including the maintenance of a non-thrombogenic intimal surface, the regulation of coagulation and fibrinolysis, immunological functions, the regulation of perfusion and permeability across the vessel walls, and the release of and response to chemical agents. Endothelial cells harvested from umbilical cord blood vessels and other sources have been used for numerous experimental purposes for many years, especially for studies on angiogenesis and its control by pharmacological manipulation, and have been well characterized. They are known by their typical cobblestone shape in monolayer culture, and their ability to form tubules when plated in three-dimensional gels and collagen sponges. Universal cellular markers for endothelial cells include the adhesion molecule CD-31 and the von Willebrand factor.

These cell types can be isolated from the umbilical cord by a variety of techniques, purified, and expanded in culture. The object of the present invention is to provide a method to isolate pure cell lines of four different cell types from a single umbilical cord. The cell lines can then be utilised in the reconstruction of multilineage tissues, including but not limited to vascular structures. These reconstructions are of interest and value not only for the study of the interactions between cells and cell types but also in a long-term therapeutic view, wherein the cells from a person's umbilical cord could be conserved and ultimately serve in the replacement of diseased or damaged tissues.

Once a suitable biopsy is taken, the four cell types are isolated and expanded to obtain purified cultures. Endothelial cells, epithelial cells, fibroblasts and smooth muscle cells can be isolated from the biopsy by techniques described herein. The invention essentially consists of enzymatic digestion in specific media and manual dissection of the umbilical cord tissue to separate the cell-containing tissues. Fibroblasts and smooth muscle cells can be harvested from tissue explants of the biopsy by cell outgrowth or by enzymatically digesting the explants and plating the digested tissue.

After the four umbilical cell types have been isolated, they must be cultured and grown into engineered tissues with sufficient mechanical stability and strength to be detached and organized into a three-dimensional living structure. Mature engineered living structures of isolated cells can include, but are not limited to, their own extracellular matrix proteins. Additional cells can be added to the four cell types at any stage of tissue formation. These cells can include additional human or animal cells or transfected or otherwise genetically modified cells.

One particular embodiment of the present invention is to provide a composition of four cell types isolated from the same autologous source and having a high progenitor potential.

An embodiment of the invention is directed to the use of neonatal progenitor cells for living or biological tissue reconstitution. There are several reasons for preferring the use of such neonatal cells to that of conventional mature cells. First, no donor is required because the cells can be obtained from neonatal umbilical cords that would otherwise be discarded. Second, in a preferred autologous system, i.e., involving use of "self" neonatal cells, the complications arising in conventional cell or tissue transplantation from the need for pretransplantation drug-induced or irradiation-induced immune incapacitation and from acute and chronic graft-versus-host disease are eliminated because, in this embodiment, neonatal cells are returned to their original owner and are therefore totally compatible. For these reasons, the present restrictions on the use of the transplantation of stem cells from different sources or tissue-derived therefrom arising from difficulties in finding even approximately matched donors, and from disease and mortality due to unavoidable genetic incompatibility, do not apply to self-reconstitution with neonatal cells.

Furthermore, the prospects of success in obtaining adequate numbers of stem cells for transplantation decline with the donor's age; although it is not clear whether the age of the donor or the patient is more important, it is proper to infer that younger (neonatal) cells are preferable for tissue reconstitution. Such neonatal cells have not been subjected to the environmental stresses that adult cells have undergone. Also, as an example of the novel medical applications which may be feasible with neonatal cells but not with conventional replacement cells available in the art, restoration with self cells taken at birth could be valuable in the treatment of disorders such as declining immune responsiveness and autoimmunity (immune reactions against one's own tissues) which occur in increasing frequency with age. In addition, the present method allows the provision of vascular cells for neovascularisation, and of fibroblastic cells for the reconstruction of mesenchymal structures such as ligament or cartilages. As well, fibroblastic cells have successfully been used in the allogeneic reconstruction of dermal tissue, and thus such allogeneic applications could equally be envisaged for the fibroblasts and other cell types of the umbilical cord.

There are additional reasons for preferring the use of neonatal cells for tissue reconstitution and engineering as provided by the present invention. The neonatal umbilical cord is a preferred source of cells for tissue reconstitution and engineering, since it is much less prone to microbial and viral contamination, known or unknown, latent or otherwise, that may be encountered in later life, other than those transmitted from the mother or during labor and delivery. In addition, in view of the extent to which the known stem cells may possibly share with other cells the limitation in the total number of cell divisions that they may undergo before senescence, it is proper to assume that the neonatal umbilical progenitor cells have a self-renewal and reconstitutional capacity that is at least as great, and perhaps even greater, than that of cells obtained at any later time in life.

The present invention will be more readily understood by referring to the following examples which are given to illustrate the invention rather than to limit its scope.

Example I

Isolation of Four Cell Types from Human Umbilical Cord

Materials and Methods

Isolation of Endothelial Cells

The umbilical cord was gently cleansed of blood and debris on the outer surface with a moist sterile gauze, and inspected for clamp marks, cuts and other analomies which might have damaged the internal structure of the cord and thus cause a mixing of the cell types extracted. An undamaged section of the umbilical cord, preferably greater than 15 cm in length, was used for the extraction of the endothelial cells. The umbilical vein on one end of the section was cannulated using a small plastic adapter, a plastic tube attached to a stopcock capable of receiving a syringe, and a circular clamp, and the vein was rinsed 3 times with 10 mL of cold sterile Hepes 1×. The remaining end was then cannulated in a like manner, and the vein rinsed again and perfused with a warm (37° C.) solution of thermolysin, 250 μg/mL in Hepes with 1 mM $CaCl_2$. An incubation of 30 minutes at 37° C. then took place, with the umbilical cord resting flat in a sterile, shallow plastic container filled with enough warm sterile Hepes+5 mM $CaCl_2$ to cover the cord. This arrangement allowed the rotation of the cord by half a turn every 5 minutes, to permit even access of the enzymatic solution to all sides of the vein. At the end of the allotted time, the cord was removed from the container and very gently massaged in order to dislodge all the endothelial cells possible. The vein was then rinsed with 30 mL warm Hepes and the perfusion liquid collected in a centrifugation tube partially filled with M199 complete medium. The cells were then pelleted by centrifugation, resuspended and plated in gelatinated culture flasks with the same medium.

Isolation of Epithelial Cells

The section of the umbilical cord used for the extraction of endothelial cells was subsequently used for the extraction of the epithelial cells. The greatest portion possible of the cord was placed in a sterile container with slots cut in opposing sides to hold the ends of the cord out of the enzymatic solution. The container was then filled as full as possible with approximately 40 mL of trypsin 0.25% EDTA, sealed and placed at 37° C. with gentle agitation for 5 min. The enzymatic solution was then discarded and replaced with a fresh aliquot. Successive incubation times of 15, 15, and 30 min. were then undertaken. After each incubation period serum was added as a trypsin inhibitor to the collected solution of trypsin, and the mixture was centrifuged. The pelleted cells from each fraction were resuspended in complete DME-Ham's 10% CS and pooled in order to perform a count of the cells obtained. The cells were seeded in culture flasks with a feeder layer of murine Swiss 3T3 irradiated fibroblasts (S3T3) (20 000 cells/$cm^2$) at a density of 80 000 cells/$cm^2$ in DME-Ham's complete medium.

Isolation of Fibroblasts from Wharton's Jelly

The section of umbilical cord from which the epithelial cells were extracted was used for the extraction of fibroblasts. Thin slices of Wharton's jelly were taken from the surface of the umbilical cord with a scalpel, taking care not to cut into the vascular structures. These slices were immediately placed in cold culture medium (DME with 10% FCS). When all the explants had been taken, they were cut into small squares (2 mm) and rinsed several times with the same medium. They were then carefully placed in gelatin-coated culture flasks with a minimum of complete medium (1.4 mL per 25 $cm^2$ flask). No changes of culture medium were done before a minimum of 4 to 5 days. Once a sufficient number of cells had migrated outwards from the explants, they were dissociated using trypsin-EDTA, centrifuged and replated in culture flasks at a density of 10 000 cells per $cm^2$.

Isolation of Smooth Muscle Cells

The same section of umbilical cord was then cut into smaller sections and used for the extraction of smooth muscle cell explants. The umbilical vein was opened with sterile scissors on the side opposing the location of the umbilical arteries. After pinning down the opened section on a dissection board with the inner vein surface uppermost, any remaining endothelial cells were removed with a moist sterile gauze. Thin strips or bands of smooth muscle tissue were detached using a sterile pair of curved jeweller's tweezers to lift them away from the surface and a scalpel to sever the ends of these strips. The explants were placed immediately in cold culture medium (DME-Ham's with 10% FCS). At the end of the procedure they were cut into small squares (2 mm) and rinsed several times with the same medium. The explants were placed in gelatin-coated culture flasks with a minimum of culture medium (1.4 mL per 25 $cm^2$ flask). No changes of culture medium were done before a minimum of 4 to 5 days. Once a sufficient number of cells had migrated outwards from the explants, they were dissociated using trypsin-EDTA, centrifuged and replated in culture flasks at a density of 10 000 cells per $cm^2$.

Maintenance of Cell Cultures

All cell cultures were maintained in their respective media, which were changed 3 times per week. Cells were passaged upon attaining a level of 80% confluence by dissociation using trypsin.

Culture Media

Endothelial cells: M199 (Sigma #5017) reconstituted with apyrogenic water and 2.2 g/L sodium bicarbonate, 20% calf serum (Hyclone), 20 mg/mL endothelial cell growth factor (Sigma E-2759), 2.28 mM glutamine (GLNS), 0.40 U/mL heparin, 100 UI/mL penicillin G, 25 mg/mL gentamycin sulphate.

Smooth muscle cells: Dulbecco-Vogt modified Eagle's medium and Ham's F12 (3:1 mixture), 10% foetal calf serum (Biomedia), 100 UI/mL penicillin G, 25 mg/mL gentamycin sulphate.

Fibroblasts: Dulbecco-Vogt modified Eagle's medium, 10% foetal calf serum (Hyclone) 100 UI/mL penicillin G, 25 mg/mL gentamicin sulphate.

Epithelial cells: Dulbecco-Vogt modified Eagle's medium and Ham's F12 (3:1 mixture), 10% calf serum (Hyclone), 10 ng/mL epidermal growth factor, 5 mg/mL insulin, 1×10-10 M cholera toxin, 5 mg/mL transferrin, 2×10-9 M 3,3', 5 triiodo-L-thyronine, 0.4 mg/mL hydrocortisone, 100 UI/mL penicillin G, 25 mg/mL gentamycin sulphate.

In other embodiments of the present invention, other extraction methods and culture media well known to those proficient in the art of cell extraction and culture may be used in place of those detailed above.

Example II

Characterisation of Cell Cultures

Cells in Culture

Figure 1:
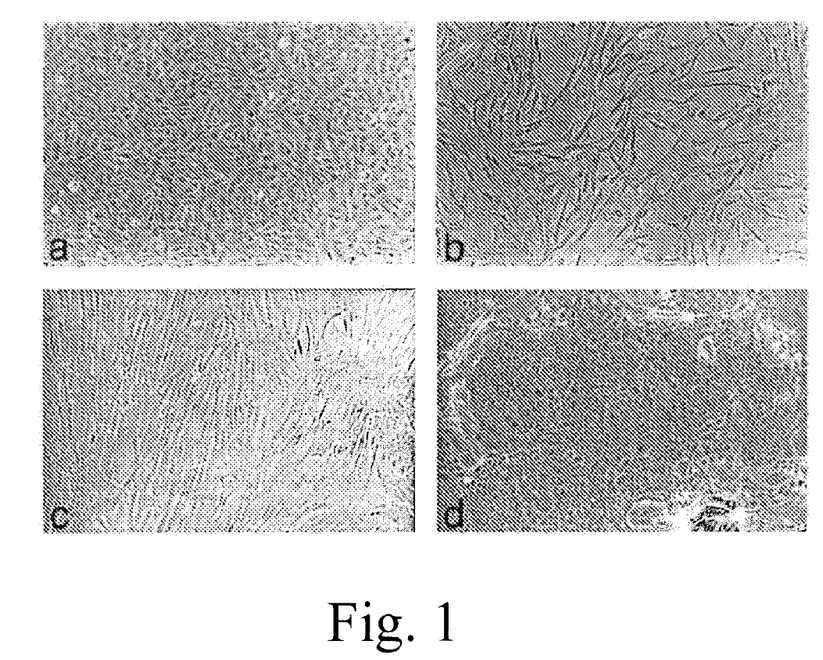
FIG. 1 illustrates the typical aspects of the four cell types in monolayer culture, in phase contrast photographs.

All four cell types could be established and maintained in culture using the aforementioned combination of extraction techniques. Each cell type has its characteristic phenotype and proliferation profile, as well as its particular requirements insofar as culture conditions. In FIG. 1, the typical aspects of the different cell types in monolayer culture are illustrated; in a) endothelial cells, in b) smooth muscle cells, in c) fibroblasts, and in d) a proliferative colony of epithelial cells surrounded by feeder S3T3 cells. All photographs were taken at 10× magnification under phase contrast.

Problems encountered with the extractions were not directly related to the extraction technique itself, but resulted from a variation of the properties of tissues and cells between different individuals. These problems included blockages in the vein which did not permit perfusion, weak spots in the vein wall which burst under pressure from the perfusion liquid, and a lack of epithelial cells due to prior handling of the umbilical cord. Other particular reasons for the failure to establish cell cultures are related to the specific cell line itself, for example unproliferative cells, and explants from which no cells or very few cells migrated.

Purity of Cell Cultures

Figure 2:
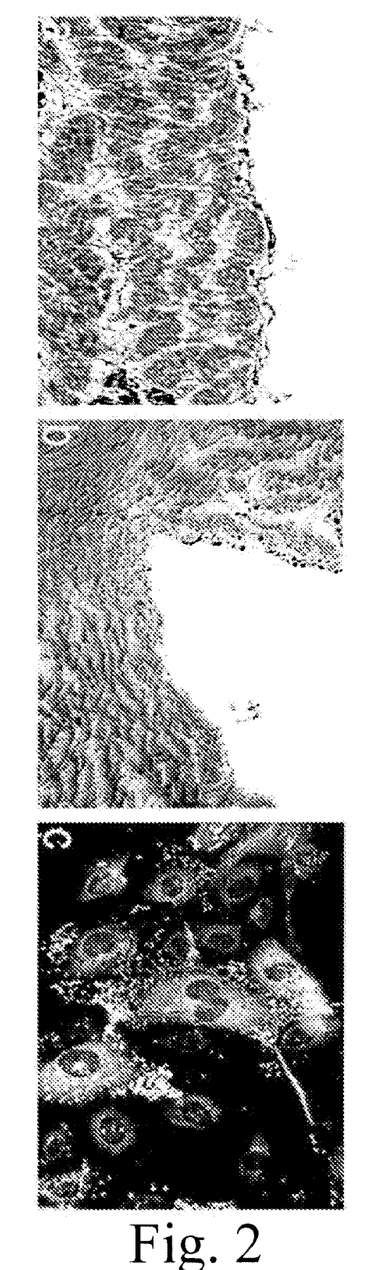
FIG. 2 illustrates sections of the umbilical cord before and after the extraction of endothelial cells, and endothelial cells in culture immunolabelled for van Willebrand factor.
Figure 3:
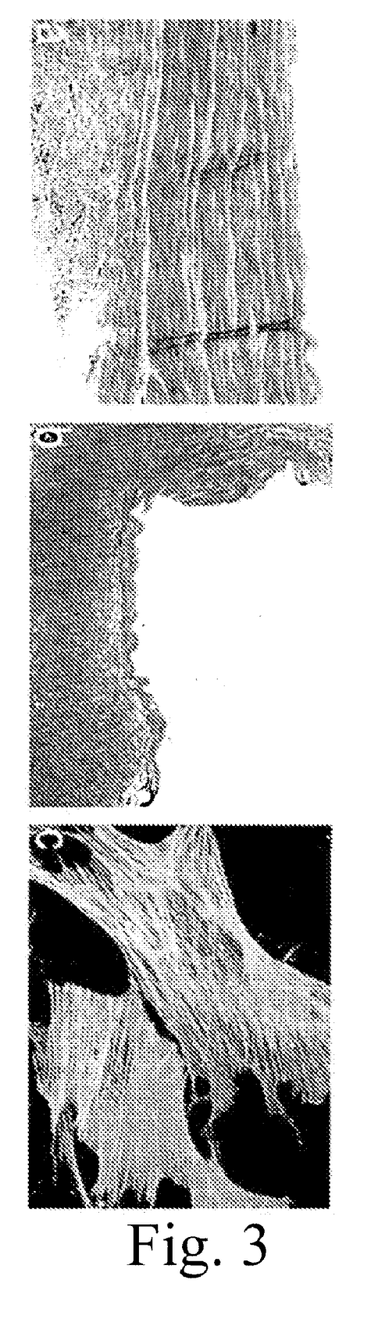
FIG. 3 illustrates sections of the umbilical cord before and after the extraction of smooth muscle cells, and smooth muscle cells in culture immunolabelled for O-smooth muscle actin.
Figure 4:
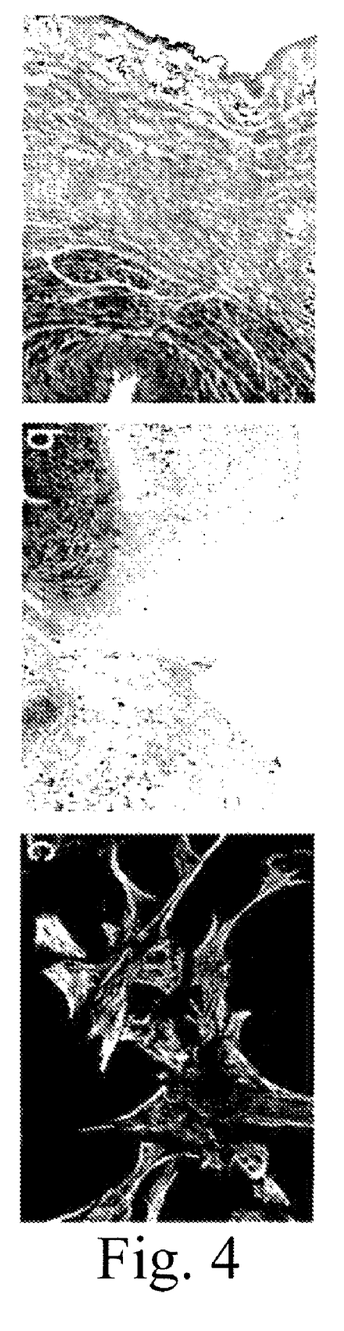
FIG. 4 illustrates sections of the umbilical cord before and after the extraction of fibroblasts, and fibroblasts in culture immunolabelled for vimentin.
Figure 5:
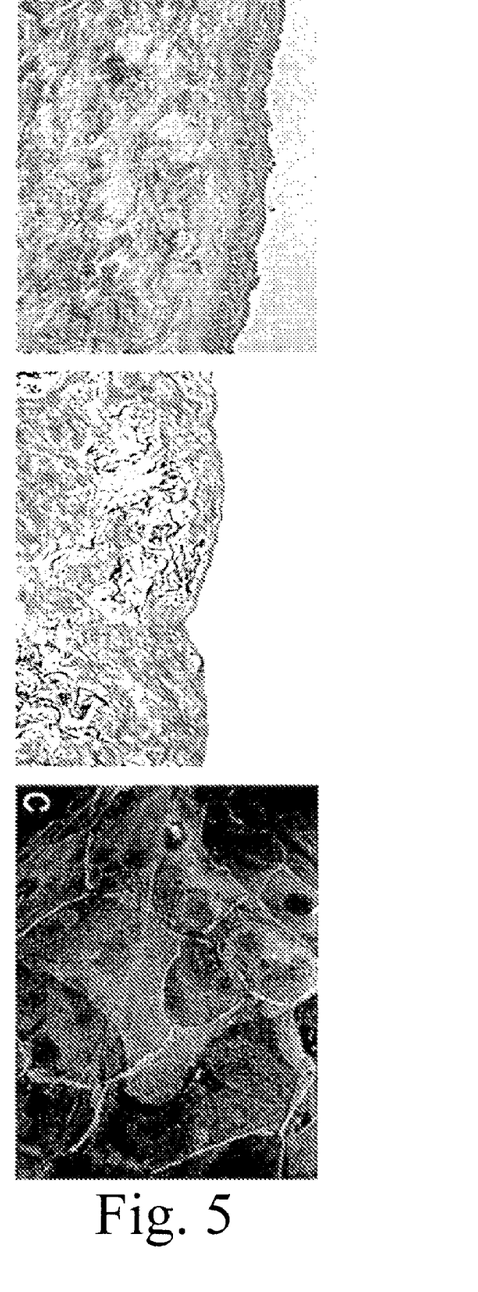
FIG. 5 illustrates sections of the umbilical cord before and after the extraction of epithelial cells, and epithelial cells in culture immunolabelled for desmoplakin.

The purity of the cell cultures obtained was verified by histological examination of sections of the umbilical cord before and after the extractions, by observation of the cells in culture, and by the presence of specific markers. The histological examination showed that no tissue was removed in the particular extractions other than that containing the cells of interest. FIG. 2a shows a section of umbilical cord vein with the layer of endothelial cells overlying the media (smooth muscle cells), at 40× magnification. After the extraction of the endothelial cells, an intact media remains (FIG. 2b, 20× magnification). FIG. 3a shows a section of umbilical cord vein with the layers of smooth muscle cells overlying the connective tissue called Wharton's jelly, 40× magnification. After extraction of the smooth muscle cells, a thin layer of media remains with no ingression into the fibroblast-populated tissue below (FIG. 3b, 20× magnification). In FIG. 4a, a section of umbilical cord shows the connective tissue called Wharton's jelly surrounding part of the umbilical cord vein, 10× magnification. After extraction of the fibroblasts, FIG. 4b shows no ingression into the media surrounding the vein (4× magnification). In FIG. 5a, a section of umbilical cord shows the epithelium overlying the connective tissue called Wharton's jelly, at 40× magnification. After extraction of the epithelial cells, FIG. 5b shows no break in the basement membrane underlying the epithelial cells and no ingression into the connective tissue of Wharton's jelly (40× magnification).

Under observation, the cells in culture displayed homogenous populations of proliferative cells with characteristic phenotypes. No cultures of mixed cell types were noted in any of the extractions studied (see FIG. 1). The identity of the cell populations was verified by immunofluorescent marking of cell type-specific protein markers in cells grown on slides and fixed in acetone. FIG. 2c shows the presence of von Willebrand factor in the endothelial cells, FIG. 3c illustrates the marking of smooth muscle α-actin in smooth muscle cells, FIG. 4c demonstrates the presence of vimentin, a structural protein common to fibroblastic cells, in the fibroblasts of Wharton's jelly (all at 40× magnification), and FIG. 5c shows the marking of desmoplakin, a protein of adhesion particular to epithelial cells, in cultured epithelial cells (60× magnification).

Characterisation of Cell Types

The endothelial cells and smooth muscle cells of the human umbilical cord have been extensively studied to date by various research groups, and details of their known characteristics can be found in many publications. Epithelial cells and the fibroblasts from Wharton's jelly, however, have received much less attention and we present here a summary of the immunofluorescent markings carried out on these two cell types both in vivo and in vitro.

TABLE 1

Characterisation of Epithelial Cells from the Human Umbilical Cord

| Marker | Umbilical Cord in vivo | Cultured Cells in vitro |
| --- | --- | --- |
| Keratin 8 | + | + |
| Keratin 10 | + | + |
| Keratin 14 | + | + |
| Keratin 16 | − | + |
| Keratin 18 | + | + |
| Keratin 19 | + | + |

TABLE 1-continued

Characterisation of Epithelial Cells from the Human Umbilical Cord

| Marker | Umbilical Cord in vivo | Cultured Cells in vitro |
| --- | --- | --- |
| Keratin 20 | − | − |
| Desmosomes | + | + |

TABLE 2

Characterisation of Fibroblasts from the Human Umbilical Cord

| Marker | Umbilical Cord in vivo | Cultured Cells in vitro |
| --- | --- | --- |
| α-Actin | + | + |
| Chondroitin sulphate | + | + |
| Collagen type I | + | − |
| Collagen type III | + | − |
| Collagen type IV | + | + |
| Collagen type V | + | + |
| Collagen type VI | + | + |
| Collagen type VII | + | − |
| Elastin | + | + |
| Fibronectin | + | + |
| Heparan Sulphate | + | − |
| Keratin 18 | + | + |
| Keratin 19 | + | + |
| Vimentin | + | + |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The invention claimed is:

1. A method for the simultaneous isolation of four cell types from one umbilical cord sample comprising the subsequent steps of:
   a) isolating endothelial cells by perfusing a vein from a section of said umbilical cord with a solution comprising thermolysin for a period of time to allow detachment of said endothelial cells from said vein;
   b) treating the section of said umbilical cord of step a) with a solution of trypsin-EDTA for a time sufficient to allow detachment and isolation of epithelial cells;
   c) mechanically removing smooth muscle cells and fibroblast-like cells from the section of said umbilical cord of step b) substantially devoid of endothelial and epithelial cells, followed by a culture period of sufficient time to allow separation and isolation of smooth muscle and fibroblast-like cells from laminae; and
   d) harvesting the isolated cells of steps a) to c).

2. The method of claim 1, wherein said cell types are progenitor cells.

3. A method for the simultaneous isolation of four cell types from one umbilical cord sample comprising the subsequent steps of:
   a) isolating endothelial cells by perfusing a vein from a section of said umbilical cord with a solution comprising at least one of thermolysin or collagenase for a period of time to allow detachment of said endothelial cells from said vein;

b) allowing the digestion of smooth muscle cells from a ring-shaped media surrounding the vein of the umbilical cord of step a) through a second perfusion with a solution comprising collagenase for a time sufficient to allow detachment of smooth muscle cells from said vein;

c) isolating epithelial cells by treating a section of said umbilical cord with a solution comprising trypsin-EDTA for a time sufficient to allow detachment of said epithelial cells; and d) isolating fibroblast like-cells by culturing a sample of a Warton's jelly layer taken from the exterior of a section of said umbilical cord in a solution comprising collagenase for a period of time sufficient to allow separation and isolation of fibroblast-like cells from said the Warton's jelly layer; and e) harvesting isolated cells of steps a) to d).

4. A method for the simultaneous isolation of four cell types from one umbilical cord sample comprising the subsequent steps of:

a) isolating epithelial cells by treating a section of said umbilical cord in a solution comprising trypsin-EDTA for a time sufficient to allow detachment of said epithelial cells;

b) mechanically removing endothelial cells from the inner surface of an umbilical cord vein of said umbilical cord sample;

c) mechanically removing smooth muscle cells from the section of step b) substantially devoid of endothelial cells, and d) mechanically removing fibroblast-like cells from the section of step c) substantially devoid of smooth muscle cells followed by a culture period of sufficient time to allow separation and isolation of smooth muscle and fibroblast-like cells from laminae; and e) harvesting the isolated cells of steps a) to e).

5. The method of claim 4, wherein said removing of step b) is performed by scraping said umbilical cord vein.

6. The method of claim 4, wherein said cell types are progenitor cells.

7. The method of claim 3, wherein said cell types are progenitor cells.

* * * * *